United States Patent [19]

Watanabe et al.

[11] Patent Number: 4,786,496

[45] Date of Patent: Nov. 22, 1988

[54] IMMUNOPOTENTIATING AGENT HAVING ANTI-TUMOR ACTIVITY

[75] Inventors: Souichirou Watanabe, Tokyo; Tadasu Fujita, Kanagawa, both of Japan

[73] Assignee: The Nisshin Oil Mills, Ltd., Tokyo, Japan

[21] Appl. No.: 830,544

[22] Filed: Feb. 18, 1986

[30] Foreign Application Priority Data

Feb. 27, 1985 [JP] Japan .................................. 60-40215

[51] Int. Cl.$^4$ .................... A61K 35/80; A61K 31/195
[52] U.S. Cl. ................................ 424/195.1; 514/560; 514/885
[58] Field of Search .................... 424/195.1; 514/558, 514/560, 885

[56] References Cited

FOREIGN PATENT DOCUMENTS 0812291  5/1979  U.S.S.R. .

OTHER PUBLICATIONS

Chem. Abstr. 97:66085r, 1982.
Chem. Abstr. 101:16909t, 1984.

*Primary Examiner*—John Rollins
*Attorney, Agent, or Firm*—Kane, Dalsimer, Sullivan, Kurucz, Levy, Eisele and Richard

[57] ABSTRACT

An immunopotentiator having an anti-tumor activity such as an effect for inhibiting the growth of tumor cells, an effect for prolonging the death by tumor, etc. is provided, which agent contains as its active ingredient, the lipid fraction or the glycolipid fraction of a marine chlorella such as *Chlorella minutissima* or *Chlorella vulgaris*, the lipid fraction being obtained e.g. by extracting a marine chlorella with an organic solvent, and the glycolipid fraction, e.g. by separating it from the lipid fraction with a mixed solvent according to silica gel chromatography.

7 Claims, No Drawings

IMMUNOPOTENTIATING AGENT HAVING ANTI-TUMOR ACTIVITY

BACKGROUND OF THE INVENTION

1. Field of the Invention

This invention relates to an immunopotentiator having an anti-tumor activity, which agent is obtaind from marine chlorellas and useful as foods, drugs, pesticides, reagents, etc.

2. Related Art Statement

A large number of anti-tumor active substances have so far been reported. Among these, a large number of substances having an anti-tumor activity through an effect of immunopoetntiator have also been reported, and main substances among these are those contained in the fungus body component of microorganisms such as bacteria, yeasts, molds, etc., fungi, etc. Further, it has been clarified that a fraction containing polysaccharides extracted from fresh water chlorellas also has a similar effect (Official gazette of Japanese patent application laid-open No. Sho 58-15920). Still further, it has also been reported that a synthetic glycolipid has an anti-tumor activity based on a similar mechanism (Japan Pharmacy Society, the 104th year's Assembly, Collected Lecture Gists, 1984).

However, the pharmacologic effect of marine microorganisms, etc. has not been studied as much till now.

SUMMARY OF THE INVENTION

The present inventors have searched for substances having an anti-tumor activity among marine microorganisms, and as a result, have found that a lipd fraction and a glycolipid fraction contained in marine chlorellas have an anti-tumor activity base on an effect of immunopotentiator.

The present invention resides in an immunopotentiator having an anti-tumor activity, which agent contains as its active ingredient, the lipid fraction or the glycolipid fraction of marine chlorellas.

DESCRIPTION OF PREFERRED EMBODIMENTS

The marine chlorellas referred to in the present invention are not limited to particular genuses and species, but usually they refer to those classified into *Chlorella minutissima*, *Chlorella vulgaris* or the like.

The lipid fraction and the glycolipid fraction of the marine chlorellas as the active ingredient of the immunopotentiator having an anti-tumor activity in the present invention can be obtained for example as follows, but the present invention should not be construed to be limited thereto:

As to the collection of the lipid fraction from marine chlorellas, a solvent such as chloroform, methanol, hexane, ethanol, etc. is added to powder of a marine chlorella in a quantity of 5 to 10 times the weight of the powder, followed by grinding the mixture, warming for 30 minutes, agitating, filtering off, further washing with an aqueous solution of Glauber's salt or the like, removing water-soluble components such as extracted sugars, dehydrating and concentrating under reduced pressure to obtain a lipid fraction.

Further, the glycolipid fraction can be obtained by subjecting the above lipid fraction to silica column chromatography, DEAE cellulose-ion exchange column chromatography on the like.

The lipid fraction or the glycolipid fraction obtained by the above operations may be treated for example by incorporating it into a liposome or the like, by making an emulsion therefrom with an emulsifier or by the like means, followed by administering the resulting substance intraperitoneouslly, by intravenous injection, or by the like means.

The present invention will be described in more detail by way of Examples, but it should not be construed to be limited thereto.

EXAMPLE 1

(Fractionation of lipid)

To powder (100 g) of a marine chlorella (*Chlorella minutissima*) was added a mixed solution of chloroform and methanol (2:1)(1 l), followed by homogenizing the mixture, warming at 40° C., for 30 minutes, agitating under nitrogen current, thereafter filtering the extraction fluid with Celite (tradename of diatomaceous earth made by Johns-Manville Company) as an auxiliary agent for filtration to remove the cell residue, adding a 6% aqueous solution of Glauber's salt (2 l) thereto, washing, separating the solvent layer, adding Glauber's salt, allowing it to stand overnight, dehydrating, filtering to remove Glauber's salt, thereafter concentrating under reduced pressure and removing the solvent to obtain a lipid fraction.

(Preparation of liposome)

The lipid fraction obtained above was mixed with yolk lecithin, cholesterol, dicetyl phosphate and α-tocopherol, followed by dissolving the mixture in a mixed solution of chloroform-methanol (2:1), concentrating the solution under reduced pressure in an eggplant type flask to remove the solvent completely, thereafter adding a 0.15M physiological saline, agitating the mixture in a Vortex Mixer for one hour, irradiating an ultrasonic wave to the resulting suspension and treating the solution till it became translucent, to obtain a liposome containing the lipid fraction obtained from the marine chlorella.

(Measurement of anti-tumor activity)

Using as an administration feed, the lipid fraction of the marine chlorella in the form of a liposome obtained above, a tumor was inoculated to ICR male mice of 6 week age intraperitoneouslly, followed by continuous administration for 7 days.

(1) Effect for inhibiting the growth of tumor cells:

Sarcoma-180 ($5 \times 10^6$ cells) was inoculated subcutaneously at the inguinal region. After the inoculation, the feed was administered in doses shown in Table 1. After 5 weeks, the respective tumors were removed and their weights were measured. The results are shown in Table 1.

(2) Effect for prolonging the death by tumor:

Erlich ($1 \times 10^5$ cells) was inoculated intraperitoneouslly. After the inoculation, the feed was administered in doses shown in Table 2 and the number of survival days was sought. The results are shown in Table 2.

(Measurement of carbon-clearance ability)

The feed (30 mg/kg) was administered intraperitoneouslly to ICR male mice continuously for 4 days. At the final date of the administration, a carbon-floating fluid (a mixture of an ink, physiological saline and a 6% aqueous solution of gelatin) (0.4 ml) was administered into the median sacral vein. Five minutes, 10 minutes and 20 minutes after the administration, respectively, blood was taken from the eyeground, and subjected to hemolysis with a 0.1% aqueous solution of Na₂CO₃ to measure the absorbance at 675 nm. The results are shown in Table 3. In addition, in any of the controls, physiological saline was administered in the same volume as that of the tested substance.

EXAMPLE 2

(Fractionation of glycolipid)

The lipid fraction obtained in Example 1 was eluted with a mixed solution of hexane-acetone (8:2) using a silica gel column, followed by removing chlorophyll, and again eluting with a mixed solution of chloroform-acetone using a silica gel column to obtain a glycolipid fraction.

As in the case of Example 1, the glycolipid fraction was incorporated into a liposome, and the resulting substance was administered to mice to measure ① inhibition of the growth of the tumor cells, ② effect for prolonging the death by tumor and ③ carbon-clearance ability. These results are shown in Tables 4, 5 and 6. The glycolipid fraction of the marine chlorella was confirmed to have a tumor-resistant effect, and it was also confirmed that a part of mice were cured completely. Further, as seen from Table 6, an immunity-activating effectiveness was observed.

TABLE 1

| Control group | Weight of tumor (mg) | | | | |
|---|---|---|---|---|---|
| | Group having the lipid fraction of marine chlorella administered (dose: mg/kg) | | | | |
| | 3 | 6 | 15 | 30 | |
| 5.9 ± 0.3 | 5.8 ± 0.2 | 4.8 ± 0.1 | 4.1 ± 0.5 | 3.2 ± 0.3 | |

One group = 10 mice (This applies also to the experiments of the succeeding Tables).

TABLE 2

| Control group | Duration to the death by tumor (day) | | | |
|---|---|---|---|---|
| | Group having the lipid fraction of marine chlorella administered (dose: mg/kg) | | | |
| | 3 | 6 | 15 | 30 |
| 9.6 ± 1.4 | 9.6 ± 2.1 | 9.7 ± 1.2 | 9.9 ± 0.8 | 12.1 ± 1.1 |

TABLE 3

| Carbon-clearance ability (Absorbance at 675 nm) | | | |
|---|---|---|---|
| Time (min.) | 5 | 10 | 20 |
| Control group | 0.792 | 0.654 | 0.047 |
| Administered group | 0.049 | 0.035 | 0.027 |

TABLE 4

| Control group | Weight of tumor (mg) | | | |
|---|---|---|---|---|
| | Group having the glycolipid fraction of marine chlorella administered (dose: mg/kg) | | | |
| | 3 | 6 | 15 | 30 |
| 6.0 ± 0.3 | 5.8 ± 0.2 | 4.2 ± 0.3 | 3.9 ± 0.4 | 2.5 ± 0.2 |

TABLE 5

| Control group | Duration to the death by tumor (day) | | | |
|---|---|---|---|---|
| | Group having the glycolipid fraction of marine chlorella administered (dose: mg/kg) | | | |
| | 3 | 6 | 15 | 30 |
| 9.7 ± 1.2 | 9.6 ± 1.8 | 9.9 ± 0.4 | 10.5 ± 1.8 | 14.6 ± 1.4 |

TABLE 6

| Carbon-clearance ability (Absorbance at 675 nm) | | | |
|---|---|---|---|
| Time (min.) | 5 | 10 | 20 |
| Control group | 0.786 | 0.648 | 0.053 |
| Administered group | 0.118 | 0.068 | 0.027 |

According to the present invention, an immunopotentiator having an effect for inhibiting the growth of tumor cells and an effect for prolonging the death by tumor can be obtained from the lipid fraction and the glycolipid fraction of marine chlorellas. Thus it is also possible to expect an effect for preventing infection of viruses, etc., from the agent.

We claim:

1. An immunopotentiating agent having anti-tumor activity, said agent containing as the active ingredient, the lipid fraction or the glycolipid fraction of a marine Chlorella selected from the group consisting of *Chlorella minutissima, Chlorella vulgaris* or mixtures thereof.

2. An agent according to claim 1 wherein said lipid fraction is a product obtained by extracting a marine chlorella with an organic solvent.

3. An agent according to claim 2 wherein said organic solvent is at least one member selected from the group consisting of chloroform, hexane, methanol, ethanol and mixtures thereof.

4. An agent according to claim 2 wherein said organic solvent is a mixed solution of chloroform with methanol.

5. An agent according to claim 1 wherein said glycolipid fraction is a product separated from the lipid fraction of a marine chlorella according to chromatography.

6. An agent according to claim 1 wherein said glycolipid fraction is a product separated from the lipid fraction of a marine chlorella with a mixed solution of hexane with acetone according to silica chromatography.

7. An agent according to claim 1 wherein said marine chlorella is *Chlorella minutissima.*

* * * * *